(12) United States Patent
Biedermann et al.

(10) Patent No.: US 8,460,595 B2
(45) Date of Patent: Jun. 11, 2013

(54) ROD-SHAPED IMPLANT, IN PARTICULAR FOR SPINAL STABILIZATION, METHOD AND TOOL FOR PRODUCING THE SAME

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 181 days.

(21) Appl. No.: 12/425,327

(22) Filed: Apr. 16, 2009

(65) Prior Publication Data

US 2009/0270922 A1 Oct. 29, 2009

Related U.S. Application Data

(60) Provisional application No. 61/048,432, filed on Apr. 28, 2008.

(30) Foreign Application Priority Data

Apr. 28, 2008 (EP) ..................................... 08008136

(51) Int. Cl.
*B29C 45/00* (2006.01)

(52) U.S. Cl.
USPC .......................... 264/328.8; 606/259; 606/261

(58) Field of Classification Search
USPC ................... 606/246–279; 264/328.8, 328.7, 264/245; 425/112, 120, 562
See application file for complete search history.

(56) References Cited

U.S. PATENT DOCUMENTS

| 4,094,952 | A | * | 6/1978 | Frank | 264/328.7 |
| 4,120,922 | A | * | 10/1978 | Lemelson | 264/40.7 |
| 4,157,883 | A | * | 6/1979 | Mares | 425/127 |
| 4,711,621 | A | * | 12/1987 | Schomblond | 425/120 |
| 5,183,096 | A | * | 2/1993 | Cook | 164/97 |
| 5,368,457 | A | * | 11/1994 | Watanabe et al. | 418/220 |
| 5,593,408 | A |  | 1/1997 | Gayet et al. |  |
| 6,099,528 | A |  | 8/2000 | Saurat |  |
| 6,102,912 | A |  | 8/2000 | Cazin et al. |  |
| 6,203,745 | B1 | * | 3/2001 | Wachsmann et al. | 264/328.7 |
| 6,562,009 | B1 |  | 5/2003 | Schöttli |  |
| 6,860,316 | B2 | * | 3/2005 | Wu et al. | 164/312 |
| 7,766,942 | B2 | * | 8/2010 | Patterson et al. | 606/261 |

(Continued)

FOREIGN PATENT DOCUMENTS

| CN | 1084469 A | 3/1994 |
| DE | 93 08 770.5 | 8/1993 |

(Continued)

OTHER PUBLICATIONS

European Search Report for European Application No. 08008136.7 in the name of Biedermann Motech GmbH, European Search Report dated Nov. 21, 2008 and mailed Dec. 3, 2008 (9 pgs.).

(Continued)

*Primary Examiner* — Jan Christopher Merene
(74) *Attorney, Agent, or Firm* — Christie, Parker & Hale, LLP

(57) ABSTRACT

A rod-shaped implant for spinal stabilization includes a first component comprising a first material, and a second component comprising a second material, wherein at least the first material is a plastic material, and wherein the first and the second component are connected by melting at least the first component to connect to the second component.

16 Claims, 6 Drawing Sheets

U.S. PATENT DOCUMENTS

| | | | |
|---|---|---|---|
| 7,828,825 B2 * | 11/2010 | Bruneau et al. | 606/260 |
| 7,871,424 B2 * | 1/2011 | Abdelgany | 606/207 |
| 7,875,059 B2 * | 1/2011 | Patterson et al. | 606/261 |
| 2004/0147928 A1 | 7/2004 | Landry et al. | |
| 2004/0215190 A1 * | 10/2004 | Nguyen et al. | 606/61 |
| 2005/0012243 A1 * | 1/2005 | Saeki et al. | 264/328.8 |
| 2005/0203513 A1 * | 9/2005 | Jahng et al. | 606/61 |
| 2005/0203517 A1 * | 9/2005 | Jahng et al. | 606/61 |
| 2005/0277922 A1 | 12/2005 | Trieu et al. | |
| 2006/0009768 A1 | 1/2006 | Ritland | |
| 2006/0142760 A1 | 6/2006 | McDonnell | |
| 2006/0242813 A1 * | 11/2006 | Molz et al. | 29/284 |
| 2006/0247638 A1 * | 11/2006 | Trieu et al. | 606/69 |
| 2006/0259117 A1 * | 11/2006 | Pal | 623/1.11 |
| 2006/0264937 A1 | 11/2006 | White | |
| 2007/0005063 A1 * | 1/2007 | Bruneau et al. | 606/61 |
| 2007/0055244 A1 | 3/2007 | Jackson | |
| 2007/0093820 A1 | 4/2007 | Freudiger | |
| 2007/0096364 A1 * | 5/2007 | Hahn et al. | 264/255 |
| 2007/0129729 A1 | 6/2007 | Petit et al. | |
| 2007/0161999 A1 | 7/2007 | Biedermann et al. | |
| 2007/0176324 A1 | 8/2007 | Taylor et al. | |
| 2007/0190230 A1 | 8/2007 | Trieu et al. | |
| 2007/0191832 A1 | 8/2007 | Trieu | |
| 2007/0225710 A1 | 9/2007 | Jahng et al. | |
| 2007/0233095 A1 | 10/2007 | Schlaepfer | |
| 2007/0270843 A1 | 11/2007 | Matthis et al. | |
| 2008/0086127 A1 * | 4/2008 | Patterson et al. | 606/61 |
| 2008/0140133 A1 | 6/2008 | Allard et al. | |
| 2008/0177388 A1 * | 7/2008 | Patterson et al. | 623/17.16 |
| 2008/0183213 A1 | 7/2008 | Veldman et al. | |
| 2008/0234744 A1 | 9/2008 | Zylber et al. | |
| 2008/0234746 A1 | 9/2008 | Jahng et al. | |
| 2008/0234754 A1 * | 9/2008 | McCarthy et al. | 606/298 |
| 2008/0262548 A1 | 10/2008 | Lange et al. | |
| 2008/0295312 A1 | 12/2008 | Molz et al. | |
| 2010/0087863 A1 * | 4/2010 | Biedermann et al. | 606/261 |

FOREIGN PATENT DOCUMENTS

| | | |
|---|---|---|
| DE | 10 2004 048 938 A1 | 10/2004 |
| EP | 1 757 243 A1 | 2/2007 |
| EP | 1 891 904 A1 | 2/2008 |
| WO | WO 2004/096066 A2 | 11/2004 |
| WO | WO 2006/037384 A1 | 4/2006 |

OTHER PUBLICATIONS

Office action for CN 200910134588.9, issued Nov. 7, 2011, 7 pages, and English translation, 7 pages.

* cited by examiner

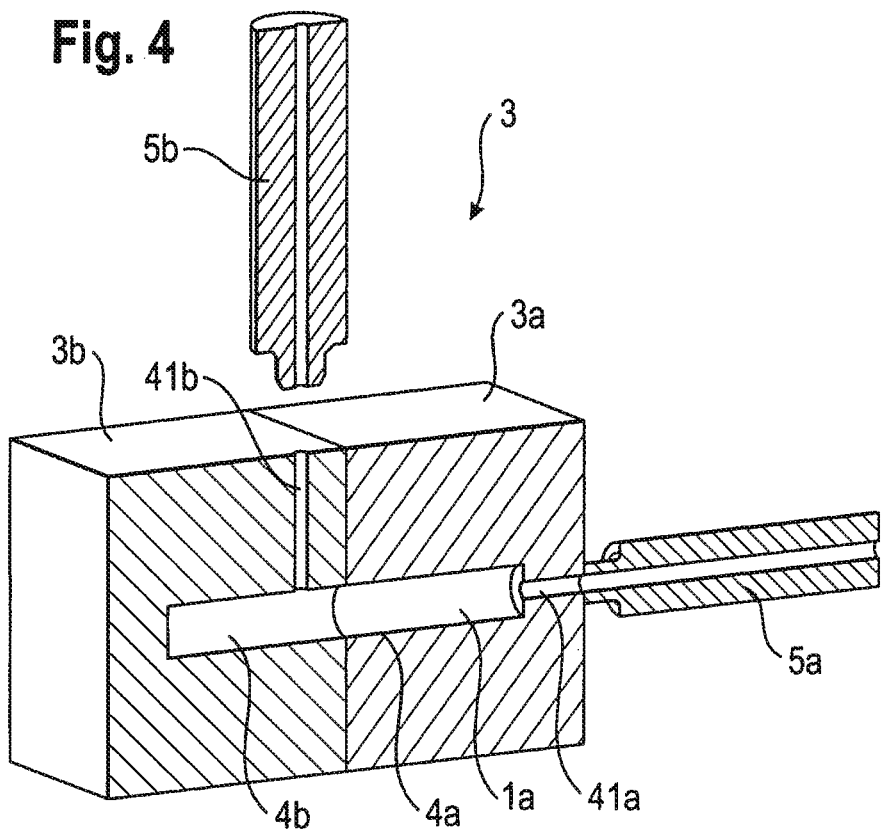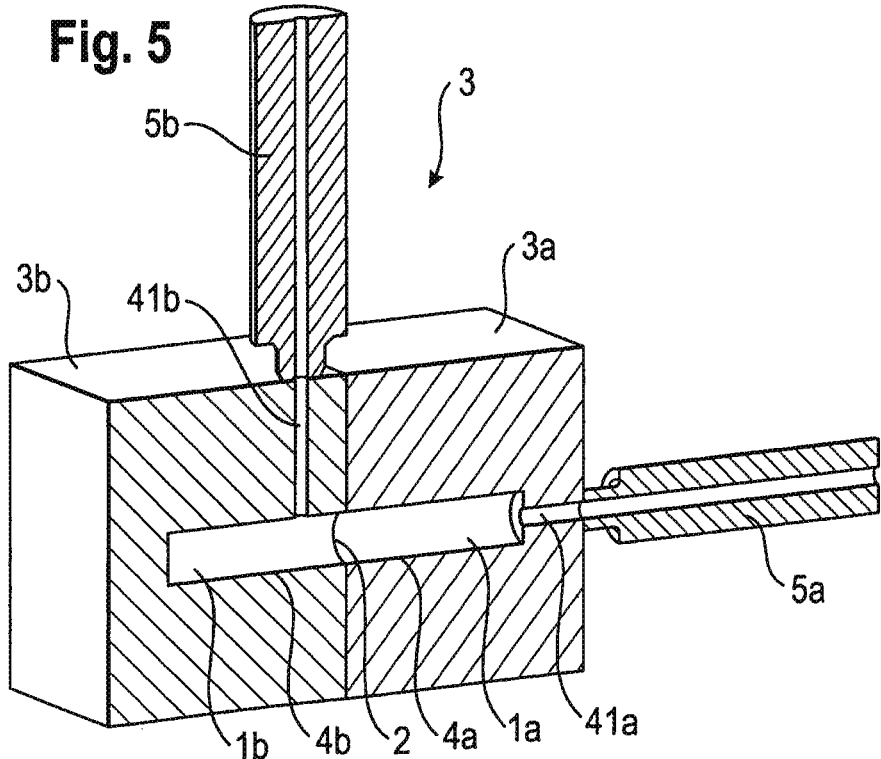

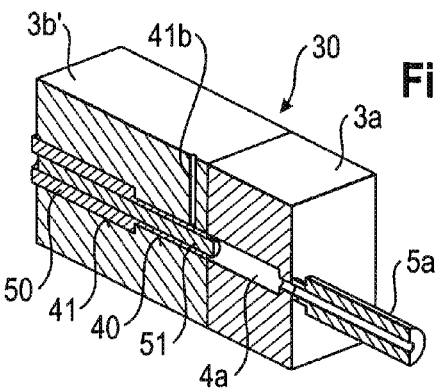
Fig. 6a
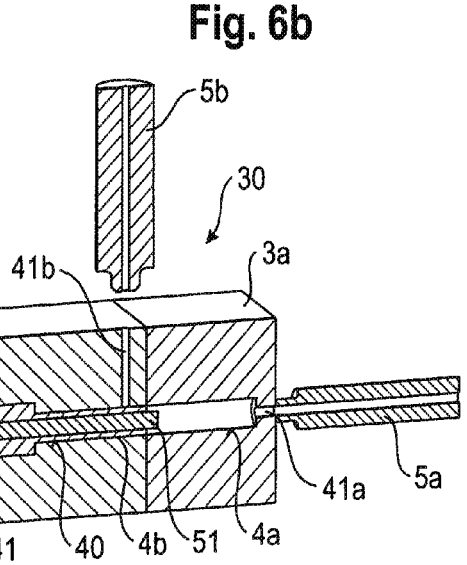
Fig. 6b
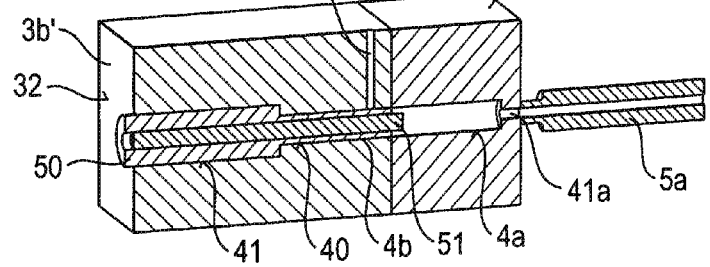
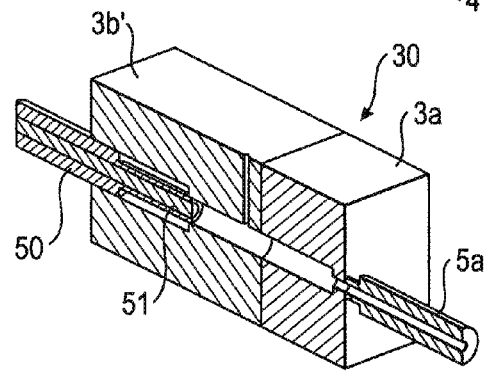
Fig. 7a
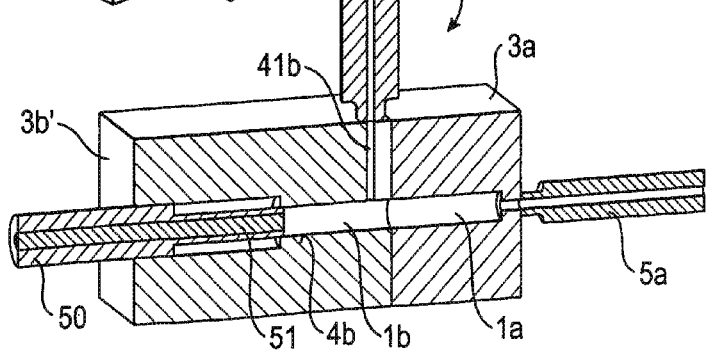
Fig. 7b

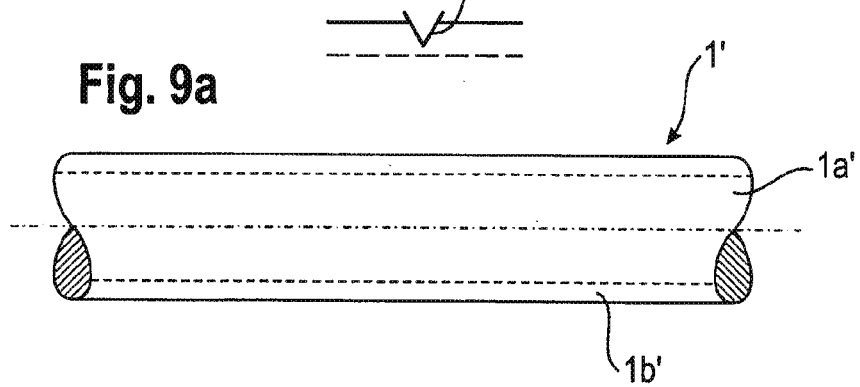
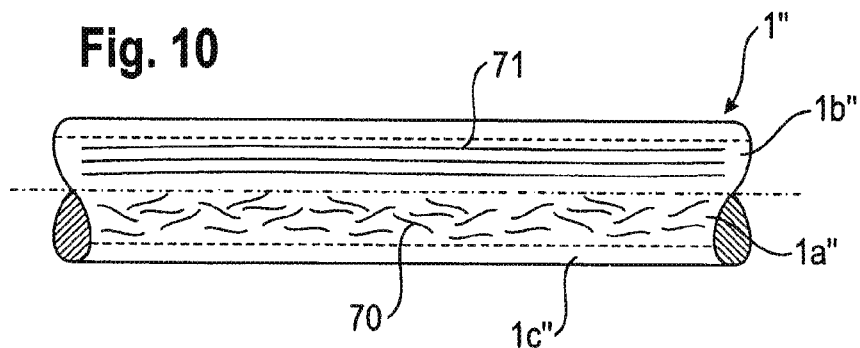
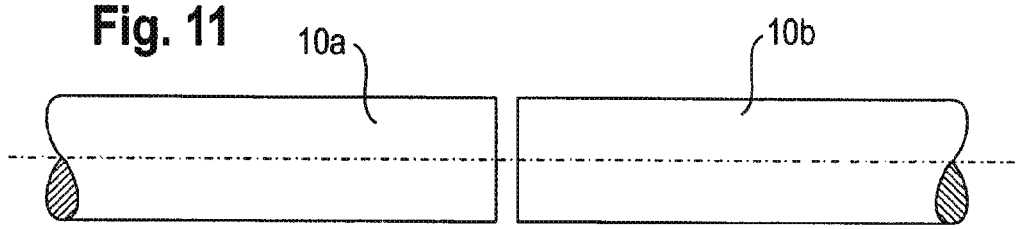
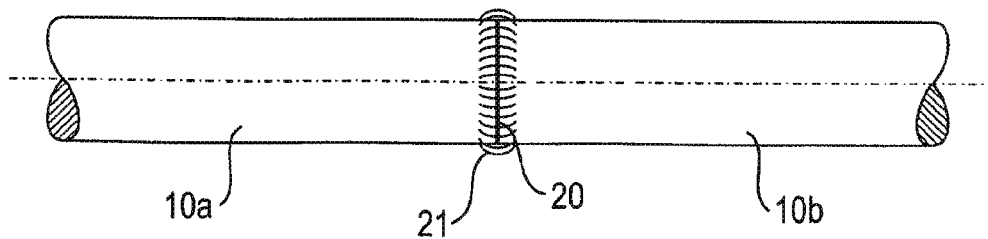

ROD-SHAPED IMPLANT, IN PARTICULAR FOR SPINAL STABILIZATION, METHOD AND TOOL FOR PRODUCING THE SAME

CROSS-REFERENCE TO RELATED APPLICATION(S)

The present application claims the benefit of U.S. Provisional Patent Application Ser. No. 61/048,432, filed Apr. 28, 2008, the contents of which are hereby incorporated by reference in their entirety, and claims priority from European Patent Application EP 08 008 136.7, filed Apr. 28, 2008, the contents of which are hereby incorporated by reference in their entirety.

BACKGROUND

The application relates to a rod-shaped implant, in particular for spinal stabilization, and to a method and a tool for producing such a rod-shaped implant.

A rod-shaped implant made of a plastic material for the dynamic stabilization of portions of the spinal column is known, for example, from US 2007/0093820 A1, US 2007/0161999 A1 and US 2007/0270843 A1.

The rod-shaped implants of the prior art are made of a plastic material having specific properties such as bending flexibility. The size of these implants, in particular their length is dimensioned such that, when anchored in the vertebrae, they extend along one or several motion segments of the spine for allowing a limited motion of the vertebrae of the respective motion segments. If a larger portion of the spine has to be stabilized several individual rods having different properties may be used for different portions of the spine.

It is further known to connect two metallic rod or a metallic rod and a flexible plastic rod with a rod connector device.

Based on the foregoing, there is a need to provide a rod-shaped implant, in particular for the stabilization of the spine, and a method and a tool for the production thereof which allows the stabilization of bone segments or motion segments of the spinal column with various degrees of flexibility along different portions of the bone segments or the spinal column.

SUMMARY OF THE INVENTION

The rod-shaped implant includes a first component having a first material and a second component having a second material, wherein at least the first material is a plastic material and wherein the first and the second component are connected by melting at least the first component to the second component. The connection between the components is non-detachable so that a single-piece rod-shaped implant is provided.

The rod-shaped implant according to the disclosure provides for portions having different properties, in particular having a different flexibility to be combined in a single-piece implant. This facilitates the handling of the implant for the surgeon because rod connectors are not needed.

Using the method according to the disclosure allows to combine different materials within a single piece rod-shaped implant which can be specially designed according to the clinical requirements.

Further features and advantages of the invention will become apparent from the following detailed description of embodiments in conjunction with the accompanying drawings.

BRIEF DESCRIPTION OF THE DRAWINGS

FIG. 4 shows the tool according to FIG. 3 in a closed state during production of the first component of the rod-shaped implant.

FIG. 5 shows the tool of FIGS. 3 and 4 in the closed state during production of the second component of the rod-shaped implant.

FIG. 6a shows a second embodiment of the tool in a perspective sectional view in a first step producing the first component of the rod-shaped implant.

FIG. 6b shows the tool of FIG. 6a in the same state in a different perspective view.

FIG. 7a shows the tool of FIG. 6a after producing of the first component in a second state.

FIG. 7b shows the tool of FIG. 7a during production of the second component in a different perspective view.

FIG. 9a shows a schematic view of a second embodiment of the rod-shaped implant.

FIG. 9b shows a schematic view of the fixation of the rod-shaped implant of FIG. 9a.

FIG. 10 shows a further embodiment of the rod-shaped implant.

FIG. 11 shows a still further embodiment of the rod-shaped implant during an intermediate step of manufacturing.

FIG. 12 shows the implant of FIG. 11 during a further intermediate step of manufacturing.

DETAILED DESCRIPTION OF THE INVENTION

Figure 1:
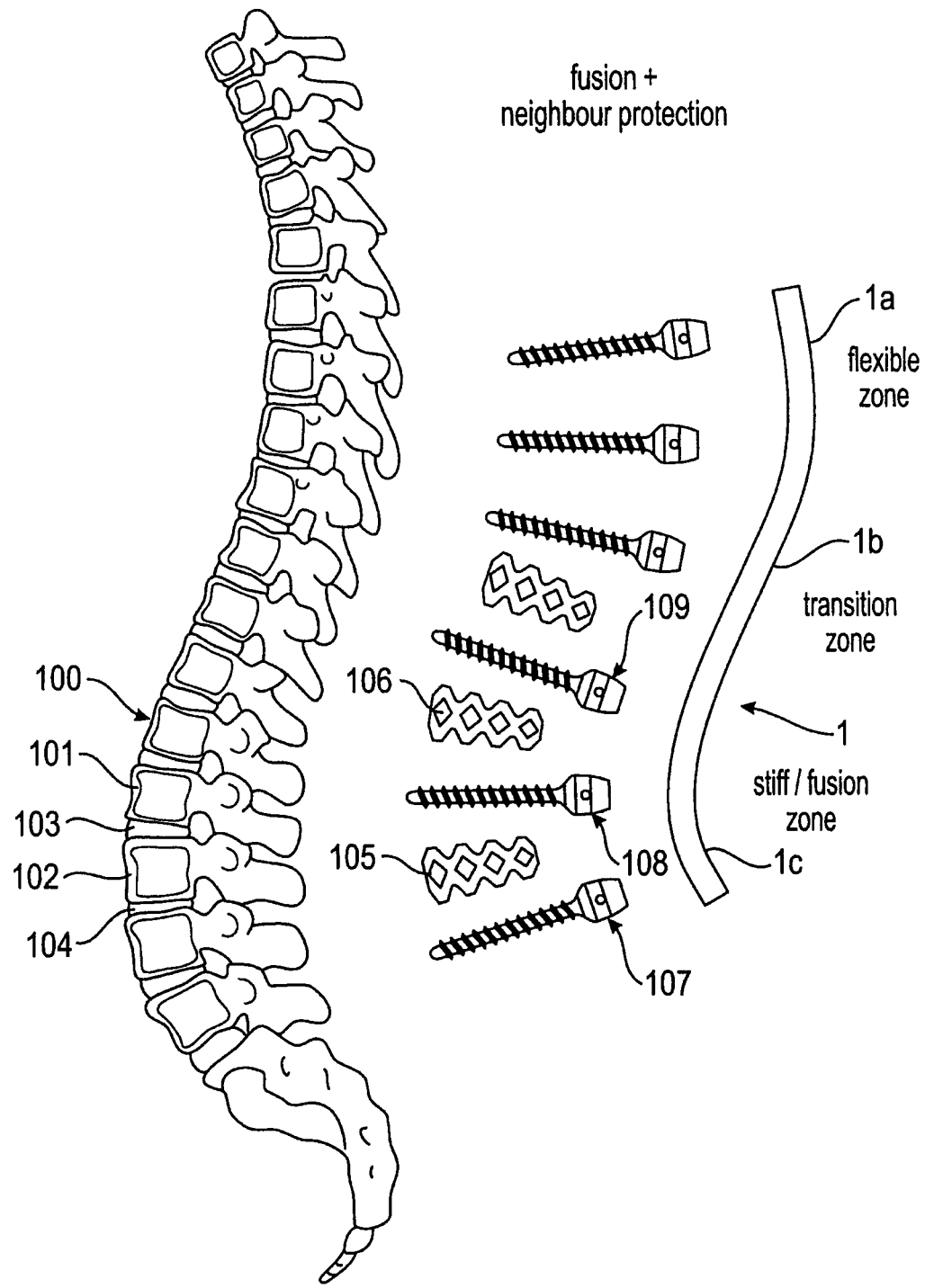
FIG. 1 shows a schematic view of the human spinal column together with a spinal stabilization and fusion system.

FIG. 1 shows a spinal column 100 with vertebrae 101, 102, etc. and intervertebral discs 103, 104, etc. In the case of seriously injured intervertebral discs the intervertebral discs are removed and the space between the vertebrae is filled with fusion cages 105, 106, etc. which may be filled with bone cement or bone graft. To fix and stabilize this system pedicle screws 107, 108, 109 are screwed into the adjacent vertebrae and a rod-shaped implant in the form of a spinal stabilization rod 1 is accommodated in the receiving portions of the pedicle screws to connect the pedicle screws to each other. The spinal stabilization rod 1 shown in FIG. 1 extends along the fusion zone having the fusion cages 105, 106 through a transition zone into a flexible zone. To fulfill the different requirements of flexibility, the spinal stabilization rod 1 includes substantially rigid portion 1c for the fixation of the fusion zone, a transition portion 1b which is less stiff than the rigid portion 1c and a flexible portion 1a which is flexible in such a way that it allows a limited motion of the motion segments stabilized thereby. With the spinal stabilization rod 1 having portions with different flexibility the vertebrae which are neighboring vertebrae to the fusion zone can be protected from overloading.

Figure 2:
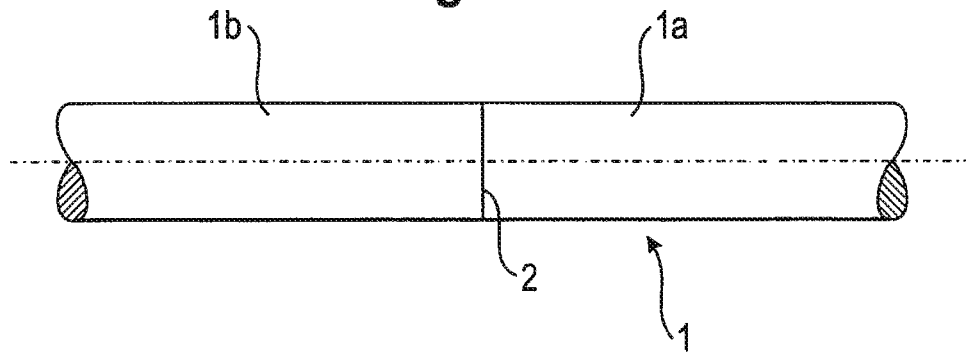
FIG. 2 shows a schematic side view of the rod-shaped implant according to a first embodiment.

The spinal stabilization rod 1 is shown in FIG. 2 with two portions 1a, 1b having different properties. In the embodiment shown the spinal stabilization rod is substantially cylindrical. The first portion 1a is made of a first material and the second portion 1b is made of a second material. The first portion 1a and the second portion 1b are connected at a connection surface 2. The first material is a bio-compatible plastic material exhibiting specific properties, in particular bending flexibility. The second material is also a bio-compatible plastic material exhibiting properties which are different from those of the first material. With reference to FIG. 1 the second portion 1b may be less flexible than the first portion 1a. Exemplary materials are PCU (poly carbonate urethane) with different degrees of hardness, for example 65 D and 55 D.

The connection surface 2 has in the embodiment shown a circular cross section. The first portion 1a is connected to the second portion 1b at the connection surface 2 by means of melting at least one of the materials of the first portion 1a or the second portion 1b. As a result thereof a permanent mechanical connection is established between the portions 1a and 1b. The connection is not detachable by loads or tension acting upon the rod under all circumstances of the intended clinical use.

The spinal stabilization rod 1 as shown in FIG. 2 is not limited to having only two portions 1a and 1b having different properties. It may have a third portion 1c as shown in FIG. 1 with high stiffness which can also be made from a bio-compatible plastic material. The rod 1 may also have alternating portions of flexible and stiff portions along the zone of the spinal column which is to be stabilized.

In use, as shown in FIG. 1, the pedicle screws are anchored into the vertebrae. Then, the spinal stabilization rod 1 is inserted into the receiving portions of the pedicle screws and fixed therein by clamping. The stabilization rod provides a rigid fixation in the fusion zone and flexibility to allow a motion of the vertebrae in the transition zone and the flexible zone with a different degree of mobility, respectively.

Figure 3:
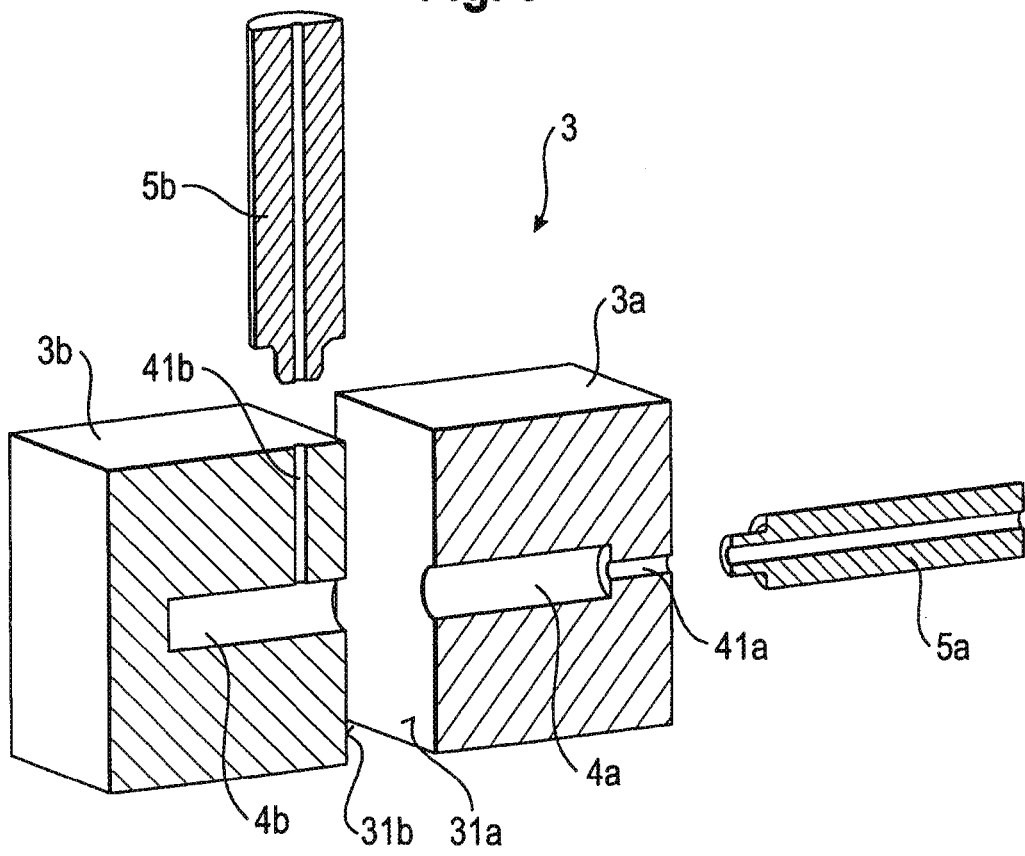
FIG. 3 shows a perspective view in section of a tool for the production of the rod-shaped implant according to FIG. 2 in an opened state.

FIG. 3 shows a tool for producing a spinal stabilization rod with two portions 1a, 1b having different properties. The tool is in an opened state and shown in cross section.

The tool 3 includes a first tool part 3a and a second tool part 3b each having a cylindrical cavity 4a, 4b which is open to respective surfaces 31a, 31b of the tool parts 3a, 3b, facing each other. The cavities 4a, 4b are dimensioned such that they define the mold pattern or die for the portions 1a, 1b of the rod 1. An injection channel 41a, 41b opens into the cavity 4a, 4b from a free surface of the first and second tool part, respectively.

The tool 3 further includes two injection nozzles 5a, 5b which are suitable for injecting molten material into the cavities 4a, 4b via the injection channels 41a, 41b.

A method for producing the spinal stabilization rod according to FIG. 2 is shown in FIGS. 4 and 5. The method uses the known technique of injection molding. For production, the tool parts 3a and 3b are closed as shown in FIG. 4. A valve or a slide (not shown) may be provided to temporarily separate cavity 4a from cavity 4b. In a first step which is shown in FIG. 4 the valve is closed and the molten first material is injected via the nozzle and the injection channel 41a into the cavity 4a.

Thereafter, the valve is opened and as shown in FIG. 5 the second material for the second portion 1b is injected via the nozzle 5b and the injection channel 41b into the cavity 4b. At the connection surface 2 where the first material encounters the second material in a molten or at least plastically deformable state a mechanical connection is established through melting which leads to the permanent connection between portion 1a and portion 1b.

After the two materials are injected and adhered together at the connection surface 2, the resulting spinal stabilization rod 1 is cooled down, if necessary by a separate cooling device (not shown), and after having reached the final solid state, the first and second tool part 3a and 3b are moved apart to open the tool 3 to take out the rod 1.

It is preferable to first inject the material for the stiffer rod portion and then to inject the material for the more flexible rod portion, but the sequence may be also changed depending on the type of material. With the process, an adjustment of the conditions necessary for injection molding of the specific materials such as temperature, time intervals, pressure etc. is possible. The adjustment can be made independently for each of the materials used.

Preferably the tool is connected to a control device which is designed to be able to control the parameters.

The tool 3 may have further tool parts if the rod has several components having different properties. The shape of the cavities and hence the shape of the rod can vary. For example, rods having any type of cross section such as square, rectangular, oval etc. can be produced.

FIGS. 6a to 7b show a second embodiment of the tool. The tool 30 according to FIGS. 6a to 7b differs from the tool 3 of the first embodiment in the design of the second tool part 3b'. The first tool part 3a is identical to the tool part 3a of the first embodiment and its description will not be repeated. Like parts of the tool 30 which correspond to the parts of tool 3 are indicated with the same reference numerals.

The cavity 4b of the second tool part 3b' has a first section 40 sized similar to the cavity 4a of the first tool part 3a and adjacent to the first section 40 a second section 41 having a larger diameter and extending to the outer surface 32.

Furthermore, a core puller 50 is provided fitting into the second section 41 of the cavity and including a core 51. The core 51 has a length which is dimensioned such that when the core puller 50 is fully inserted into the second section 41 the core 51 extends into the first cavity 4a of the first tool part 3a to a certain extent.

In the production of the rod 1, as shown in FIGS. 6a and 6b, first, the tool is closed and the core puller 50 is pushed into the second cavity 4b such that the core 51 extends into the first cavity 4a. Then molten first material is injected via the nozzle 5a and the injection channel 41a into the first cavity thereby surrounding the end portion of the core 51.

Thereafter, as shown in FIGS. 7a and 7b the core puller 50 is retracted and the second material is injected via the nozzle 5b and the injection channel 41b into the second cavity 4b. The molten second material flows into the first cavity 4a to the portion which was occupied by the end portion of end core 51 during the injection molding step of the first material. Accordingly, the surface area of the connection surface 2 can be enhanced which leads to an increased strength of the connection.

Figure 8A:
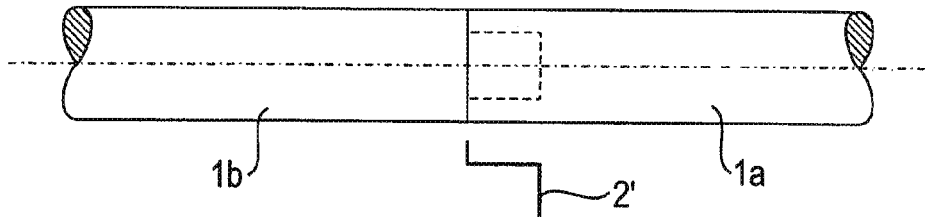
FIG. 8a to FIG. 8e show modifications of the rod-shaped implant of FIG. 2 wherein the surface of contact of the first component and the second component is increased.
Figure 8B:
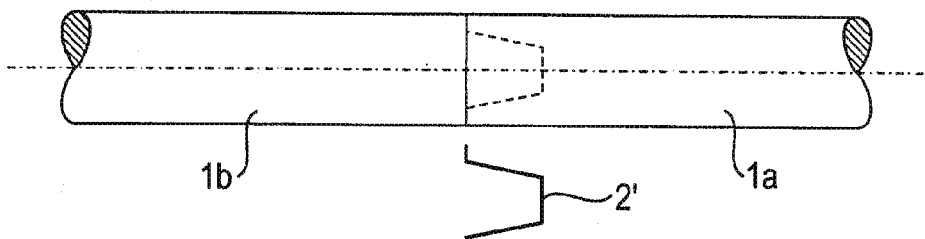
Figure 8C:
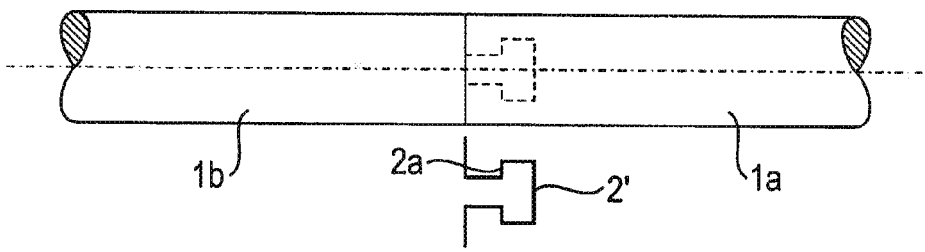
Figure 8D:
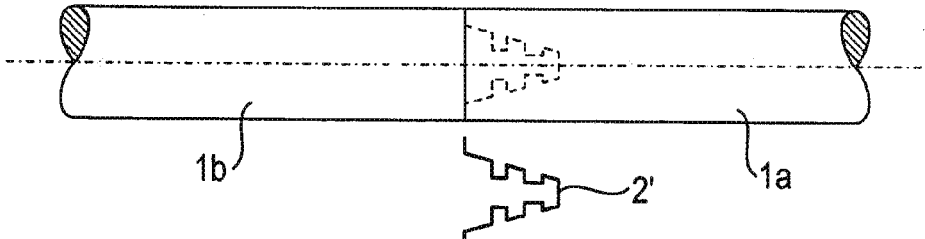
Figure 8E:
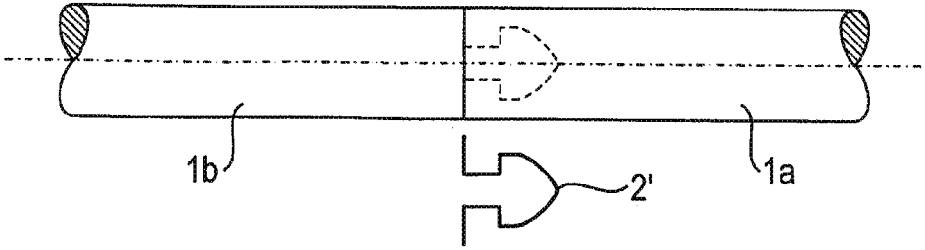

FIGS. 8a to 8e show various shapes with increased surface area of the connection surface 2' by providing a core 51 with a corresponding shape. FIG. 8a shows a cylindrical connection surface 2, FIG. 8b shows a connection surface having a truncated cone shape, FIG. 8c shows a connection surface having an undercut 2a. FIG. 8d shows a connection surface with a christmas-tree-shape and FIG. 8e shows a connection surface having a tree-shape with an undercut. However, other shapes are conceivable.

FIG. 9a shows a second embodiment of the spinal stabilization rod. The spinal stabilization rod 1' differs from the spinal stabilization rod 1 according to FIG. 2 in that the two components 1a' and 1b' having different properties are not connected at a front side of the cylindrical rod but are connected along the whole outer surface. The first component 1a' forms an inner cylinder and the second component 1b' forms an outer hollow cylinder connected to the inner cylinder at the surface. In this case, component 1a' is comprised of a stiffer material whereas the second component 1b' is comprised of a material having a lesser degree of stiffness or hardness. For example, the first component 1a' can be made of plastic material having a degree of hardness of 65 D and the second component is made of a material having a degree of hardness of 55 D. This rod can be used in particular in such applications where the stiffer component 1a' has to provide a high degree of tension stiffness for fusion. However, such a stiffer rod is hardly fixable in the receiving portion of the pedicle screw. With the embodiment according to FIG. 9a any clamping device, such as a clamping tooth or projection 60 as shown in FIG. 9b, can penetrate into the more flexible material. This results in a secure clamping.

FIG. 10 shows a third embodiment of the spinal stabilization rod. The spinal stabilization rod 1" comprises in radial direction several zones 1a", 1b, 1b", 1c" having different properties. For example, zone 1a" can comprise fibers 70 to provide a specific stiffness. Zone 1b" can have oriented fibers 71 and zone 1c" is comprised of a material with a lesser degree of stiffness. The tool required for the production thereof is adapted to form the rod with different zones by injection molding of different materials to connect them at the surface area by melting. Any combination and shape of zones is conceivable.

The invention is not limited to plastic materials. It is applicable also for a rod-shaped implant comprising a first component made of a metallic material and a second component made of a plastic material which is melted to engage the metallic material at a connection surface.

The invention is further not limited to be used with a specific type of pedicle screw. Any type of known bone anchors, for example monoaxial and polyaxial screws can be used. A still further embodiment is shown in FIGS. 11 and 12. As can be seen in FIG. 11, the rod-shaped implant includes of rod-parts 10a, 10b which are made of different materials, similar to the implants of foregoing embodiments. The rod parts are prefabricated. The implant is manufactured by welding the rod parts together at the connection surface 20, which is one end surface of the rod parts. For the welding technique ultrasound welding or infrared welding are preferable, but any other welding technique can also be used. With welding, a permanent connection between the rod parts is established through melting. As can be seen in FIG. 12, a bulge 21 of material usually appears in the course of the manufacturing procedure which results from the flow of the material during the welding step. In a still further manufacturing step this bulge is removed by a post treatment, such as, for example, grinding.

What is claimed is:

1. A combination comprising a rod-shaped implant for spinal stabilization and a tool for producing the rod-shaped implant,
wherein the rod-shaped implant comprises:
a first component comprising a first material, the first component having a first end and a second end spaced from the first end;
a second component connected to the first component and comprising a second material different from the first material, the second component extending from the second end of the first component in a direction away from the first end of the first component;
wherein at least the first material is a plastic material;
wherein the connection between the first component and the second component consists of a melted connection; and
wherein the first component and the second component are injection molded; and
wherein the tool comprises:
a first tool part with a first cavity for forming the first component of the rod-shaped implant;
a second tool part with a second cavity for forming the second component of the rod-shaped implant; and
a stop;
wherein when the first tool part and the second tool part are assembled together, the first cavity and the second cavity respectively have openings facing one another, and the stop is moveable between a first position where one of the first cavity or the second cavity is isolated from the other one of the first cavity or the second cavity, and a second position where the first cavity and the second cavity are connected and define a shape of the rod-shaped implant; and
wherein the stop comprises a core configured to form a cavity within one of the components.

2. The combination according to claim 1, wherein the second component comprises a plastic material which is different from the first material.

3. The combination according to claim 1, wherein the second component comprises a metal.

4. The combination according to claim 1, wherein the first component is a first rod and the second component is a second rod, wherein the first rod and the second rod are connected at one of their ends.

5. The combination according to claim 1, wherein one component surrounds at least a portion of the other component.

6. The combination according claim 1, wherein one of the components has a portion with an increased surface area for connection with the other component.

7. The combination according to claim 1, wherein the plastic material comprises stiffening elements.

8. The combination according to claim 7, wherein the stiffening elements are fibers.

9. The combination according to claim 1, wherein a cross-sectional shape of the first component is the same as a cross-sectional shape of the second component at the melted connection.

10. The combination according to claim 1, wherein the tool further comprises:
a first injection nozzle for injecting molten first material into the first cavity to form the first component of the rod-shaped implant; and
a second injection nozzle for injecting molten second material into the second cavity to form the second component of the rod-shaped implant;
wherein the melted connection between the first component of the rod-shaped implant and the second component of the rod-shaped implant is configured to be formed where the openings of the first cavity and the second cavity meet when the first and second tool parts are assembled together.

11. The combination according to claim 1, wherein when the core is in the first position, the core is positioned in one of the first cavity or the second cavity while protruding into the other one of the first cavity or the second cavity.

12. A method for producing a rod-shaped implant for spinal stabilization by utilizing a tool, the rod-shaped implant comprising a first component comprising a first material, the first component having a first end and a second end spaced from the first end, a second component connected to the first component and comprising a second material different from the first material, the second component extending from the second end of the first component in a direction away from the first end of the first component, wherein at least the first material is a plastic material, wherein the connection between the first component and the second component consists of a melted connection, and wherein the first component and the second component are injection molded, and the tool comprising a first tool part with a first cavity for forming the first component of the rod-shaped implant; a second tool part with a second cavity for forming the second component of the rod-shaped implant; and a stop; wherein when the first tool part and the second tool part are assembled together, the first cavity and the second cavity respectively have openings facing one another, and the stop is moveable between a first position where one of the first cavity or the second cavity is isolated from the other one of the first cavity or the second cavity, and a second position where the first cavity and the second cavity are connected and define a shape of the rod-shaped implant; and wherein the stop comprises a core configured to form a cavity within one of the components, the method comprising:

injection molding the first component;

injection molding the second component; and connecting the first component and the second component by melting the first component to the second component.

13. The method according to claim 12, wherein the second material is a plastic material which is different from the first material.

14. The method according to claim 13, wherein the first component is welded to the second component.

15. A tool for producing a rod-shaped implant for spinal stabilization, the tool comprising:

a first tool part with a first cavity for forming a first component of a rod-shaped implant;

a second tool part with a second cavity for forming a second component of a rod-shaped implant; and a stop;

wherein when the first tool part and the second tool part are assembled together, the first cavity and the second cavity respectively have openings facing one another, and the stop is moveable between a first position where one of the first cavity or the second cavity is isolated from the other one of the first cavity or the second cavity, and a second position where the first cavity and the second cavity are connected and define a shape of a rod-shaped implant; and wherein the stop comprises a core, and wherein when the core is in the first position, the core is positioned in one of the first cavity or the second cavity while protruding into the other one of the first cavity or the second cavity.

16. The tool according to claim 15, further comprising:

a first injection nozzle for injecting molten first material into the first cavity to form a first component of a rod-shaped implant; and a second injection nozzle for injecting molten second material into the second cavity to form a second component of a rod-shaped implant;

wherein a connection between a first component and a second component of a rod-shaped implant is configured to be formed where the openings of the first cavity and the second cavity meet when the first and second tool parts are assembled together.

* * * * *

UNITED STATES PATENT AND TRADEMARK OFFICE
CERTIFICATE OF CORRECTION

PATENT NO. : 8,460,595 B2  
APPLICATION NO. : 12/425327  
DATED : June 11, 2013  
INVENTOR(S) : Lutz Biedermann et al.

Page 1 of 1

It is certified that error appears in the above-identified patent and that said Letters Patent is hereby corrected as shown below:

In the Claims

| | |
|---|---|
| Column 6, Claim 6, line 27 | After "according" |
| | Insert -- to -- |
| Column 8, Claim 15, line 1 | Delete "fonning" |
| | Insert -- forming -- |

Signed and Sealed this  
Twentieth Day of May, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,460,595 B2 | Page 1 of 1 |
| APPLICATION NO. | : 12/425327 | |
| DATED | : June 11, 2013 | |
| INVENTOR(S) | : Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this
Sixteenth Day of December, 2014

Michelle K. Lee
*Deputy Director of the United States Patent and Trademark Office*